United States Patent [19]

Hrib et al.

[11] Patent Number: 5,036,152
[45] Date of Patent: Jul. 30, 1991

[54] ALKOXYCARBONYLALKYLPHOSPHOLIPIDS AND ALKYLAMINOCARBONYLALKYLPHOSPHOLIPIDS

[75] Inventors: Nicholas J. Hrib, Somerville; Kirk D. Shoger, Piscataway; John J. Tegeler, Bridgewater, all of N.J.

[73] Assignee: Hoechst-Roussel Pharmaceuticals Incorporated, Somerville, N.J.

[21] Appl. No.: 403,892

[22] Filed: Sep. 5, 1989

Related U.S. Application Data

[62] Division of Ser. No. 116,285, Mar. 10, 1988, Pat. No. 4,888,328.

[51] Int. Cl.$^5$ ............... C07D 295/04; C07D 295/084; C07D 277/04; C07F 9/09
[52] U.S. Cl. ..................................... 544/57; 558/117; 558/86; 558/172; 544/108; 544/337; 544/157; 544/110; 548/112; 548/116; 548/117; 548/413; 546/22; 546/24; 514/90
[58] Field of Search ................. 544/57, 108, 337, 157; 546/22; 548/112, 116, 117; 558/117; 514/76, 79, 85, 89, 92

[56] References Cited

U.S. PATENT DOCUMENTS

| | | | |
|---|---|---|---|
| 4,119,714 | 10/1978 | Kay et al. | 424/199 |
| 4,159,988 | 7/1979 | Eibl et al. | 260/340.9 |
| 4,163,748 | 8/1979 | Eibl et al. | 260/403 |
| 4,372,949 | 2/1983 | Kodama et al. | 424/199 |
| 4,492,659 | 1/1985 | Boises et al. | 260/925 |

FOREIGN PATENT DOCUMENTS

| | | |
|---|---|---|
| 0769532 | 1/1972 | Belgium . |
| 0040039 | 11/1981 | European Pat. Off. . |
| 0050460 | 3/1982 | European Pat. Off. . |
| 0138558 | 3/1985 | European Pat. Off. . |
| 0138559 | 3/1985 | European Pat. Off. . |
| 2009341 | 9/1971 | Fed. Rep. of Germany . |
| 2009342 | 9/1971 | Fed. Rep. of Germany . |
| 2033357 | 1/1972 | Fed. Rep. of Germany . |
| 2619686 | 11/1977 | Fed. Rep. of Germany . |
| 2619715 | 11/1977 | Fed. Rep. of Germany . |
| 138216 | 10/1979 | German Democratic Rep. . |

OTHER PUBLICATIONS

Chem. Abst. 83(1):7459d (1975), Natarajan et al.
Chem. Abst. 96(13):103584e (1982), of B. Berthon, et al., Abst. of Tetrahedron Letters, 22 (41), 4073 (1981).
Kauffman, Chem. Abst. 72(6):22266e (1970).
Chem. Abst. 68(17):77776u of Japanese Patent 13,927 (76) (1968), Iwakura et al.
Chem. Abst. 96(11):85029w of M. R. Thissen, et al., (1982) of Organic Preparations and Procedures Int., 12(6), 337(1980).
M. S. Chandrakumar et al., Biochimica et Biophysica Acta, 711(1982) 357–360.
Chandrakumar et al., Tetrahedron Letters, vol. 22, No. 31, pp. 2949–2952 (1981).
A. Wissner et al., Journal of Medicinal Chemistry (1986), vol. 29, No. 3, pp. 328–334.
M. L. Lee, INSERM Symposium No. 23, J. Benveniste and B. Arnoux, Editors, Elsevier Science Pub. BV, p. 49 (1983).
M. Ohno, et al., INSERM Symposium No. 23, J. Benveniste and B. Arnoux, Editors, Elsevier Science Pub. BV, p. 9, 1983.
L. M. Van Deenen and G. H. DeHaas, Biochemica et Biophysica Acta, 70, 538 (1963).
F. Heymans, et al., Biochimica et Biophysica Acta, 666, 230(1981).
H. S. Hendrickson, et al., Journal of Lipid Research, 24, 1532 (1983).
P. P. M. Bonsen, et al., Biochemica et Biophysica Acta, 270, 364 (1972).

Primary Examiner—John M. Ford
Attorney, Agent, or Firm—Elliott Korsen

[57] ABSTRACT

Novel alkoxycarbonylalkylphospholipids, alkylaminocarbonylalkylphospholipids, processes for the preparation thereof, and methods for treating inflammation utilizing compounds or compositions thereof are disclosed.

3 Claims, No Drawings

ALKOXYCARBONYLALKYLPHOSPHOLIPIDS AND ALKYLAMINOCARBONYLALKYLPHOSPHOLIPIDS

This is a division of application Ser. No. 116,285 filed 3/10/88, now U.S. Pat. No. 4,888,328 issued Dec. 19, 1989.

This invention relates to alkoxycarbonylalkylphospholipids and alkylaminocarbonylalkylphospholipids. More particularly, this invention relates to phospolipids of the formula:

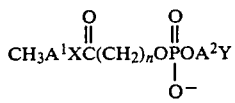

FORMULA I wherein $A^1$ is a bivalent radical of the formula $-C_mH_{2m}-$ wherein m is an integer having a value from 0 to 20, inclusive; $A^2$ is a bivalent radical of the formula $-C_pH_{2p}-$ wherein p is an integer having a value from 2 to 6, inclusive; X is a bivalent radical of the formula $-O-$ or $-N(R)-$ wherein R is selected from the group consisting of hydrogen, alkyl radicals having up to six carbon atoms, inclusive, and phenyl radicals of the formula

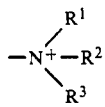

wherein a is an integer having a value from 0 to 3, inclusive, and
Z is selected from the group consisting of alkyl radicals having 1 to 6 carbon atoms, inclusive, alkoxy radicals having 1 to 6 carbon atoms, inclusive, halogen, hydroxy, and trifluoromethyl radicals, wherein for each value of a, Z may be the same or different; Y is

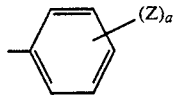

wherein $R^1$ is an alkyl radical having up to six carbon atoms, inclusive and $R^2$ and $R^3$ are independently alkyl radicals having up to six carbon atoms, inclusive, or, taken together with $R^1$ and the nitrogen atom to which they are attached form a group of the formula

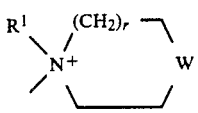

wherein r is 0 or 1, W is oxygen, $CH_2$, sulfur or $N(R^4)$ wherein $R^4$ is an alkyl radical having up to 6 carbon atoms, inclusive or aryl; and n is an integer having a value of 3 or 4; the geometrical isomers, or optical antipodes thereof, which are useful as antiinflammatory agents alone or in combination with one or more adjuvants.

Preferred alkoxycarbonylalkylphospholipids and alkylaminocarbonylalkylphospholipids of this invention are compounds of the formula:

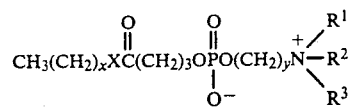

FORMULA II wherein X is a bivalent radical of the formula $-O-$ or $-N(H)-$; $R^1$ is an alkyl radical having up to 6 carbon atoms, inclusive; $R^2$ and $R^3$ are independently alkyl radicals having up to six carbon atoms, inclusive, or taken together with $R^1$ and the nitrogen atom to which they are attached form a group of the formula

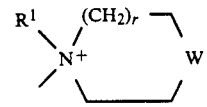

wherein r is 0 or 1, and W is oxygen, $CH_2$, sulfur or $N(R^4)$ wherein $R^4$ is an alkyl radical having up to 6 carbon atoms, inclusive or aryl; x is an integer having a value from 0 to 20, inclusive; and y is an integer having a value from 2 to 6 inclusive; the geometrical isomers or optical antipodes thereof.

Subgeneric to the phospholipids of this invention are compounds wherein:
(a) X is $-O-$;
(b) X is $-N(R)-$ wherein R is a phenyl radical of the formula

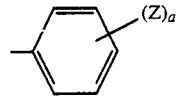

wherein a is an integer having a value from 0 to 3, inclusive, and Z is selected from the group consisting of alkyl radicals having 1 to 6, preferably 1 to 3, carbon atoms, inclusive, alkoxy radicals having 1 to 6, preferably 1 to 3, carbon atoms, inclusive, halogen, preferably fluorine or chlorine, hydroxy, and trifluoromethyl radicals; wherein for each value of a, Z may be the same or different;
(c) X is $-N(H)-$;
(d) X is $-N(R)-$ wherein R is an alkyl radical having up to 6 carbon atoms inclusive;
(e) Y is

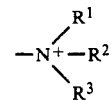

wherein $R^1$, $R^2$ and $R^3$ are independently alkyl radicals having up to 6 carbon atoms, inclusive; and
(f) Y is

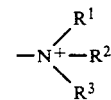

wherein R$^1$ is an alkyl radical having up to 6 carbon atoms inclusive, and R$^2$ and R$^3$ together with R$^1$ and the nitrogen atom to which they are attached form a group of the formula:

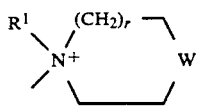

wherein W is oxygen, CH$_2$, sulfur or N(R$^4$) wherein R$^4$ is an alkyl radical having up to 6 carbon atoms, inclusive or aryl; and r is 0 or 1.

As used herein the term "alkyl" refers to a straight or branched chain hydrocarbon radical containing no unsaturation, such as, for example methyl, ethyl, 1-propyl, 2-propyl, 1-butyl, 1-pentyl, 2-pentyl, 3-hexyl and the like the term "alkoxy" refers to a monovalent substituent which consists of an alkyl group linked through an ether oxygen and having its free valence bond from the ether oxygen such as, for example methoxy, ethoxy, 1-and 2-propoxy, 1-butoxy, 1,2-dimethylethoxy, 1- and 2-pentoxy-, 3-hexoxy- and the like; the term "aryl" refers to a phenyl radical optionally substituted by one or more substituents selected from the group consisting of alkyl, alkoxy, halogen, hydroxy or trifluoromethyl; the term "halogen" refers to a member of the family of fluorine, chlorine, bromine or iodine; and the term "alkanol" refers to a compound formed by a combination of an alkyl group and a hydroxy radical such as, for example methanol, ethanol, 1- and 2-propanol, t-butanol, and the like.

The alkoxycarbonylalkylphospholipids and alkylaminocarbonylalkyl phospholipids of this invention are synthesized by the processes illustrated in Reaction Schemes A, B, and C.

As shown by Reaction Scheme A, Formula I alkylaminocarbonylalkylphospholipids and alkoxycarbonylalkylphospholipids wherein n is 3 and A$^2$ is —(CH$_2$)$_2$— are produced by reacting an alkanol or alkylamine 1 with gamma-butyrolactone 2 to produce an alkyl 4-hydroxy- butyrate or butyramide 3 which is reacted with 2-chloro-2-oxo-1,3,2-dioxaphospholane to form a cyclic triester 4 which in turn is converted to an inner salt 6 by reaction with a tertiary amine 5.

The reaction between the alkanol or alkylamine 1 and gammabutyrolactone is generally conducted in the presence of an inert organic solvent (e.g. aromatic hydrocarbons such as benzene, toluene, xylene, and the like; toluene being preferred) at a temperature of from about 50° to the reflux temperature of the solvent medium. Preferably, the reaction is conducted under nitrogen at reflux temperature. In order to promote the reaction, the use of an appropriate catalyst is recommended (e.g. p-toluenesulfonic acid, zinc chloride).

The phosphorylation of the alkyl 4-hydroxybutyrate or alkyl 4-hydroxybutyramide 3 by reaction with 2-chloro-2-oxo-1,3,2-dioxaphospholane is generally conducted under anhydrous conditions at a temperature of from about 0° to about 100° C. in the presence of an inert organic solvent. Preferred temperatures for the phosphorylation reaction range from about 0° to about 30° C. Suitable solvents includes ethereal solvents such as, for example, diethyl ether, tetrahydrofuran, dioxane, dimethoxyethane and the like, aromatic hydrocarbons such as benzene, toluene, xylene and the like, halocarbons such as chloroform, methylene chloride, and the like, and mixtures thereof. The reaction is optionally conducted in the presence of an acid acceptor. Among the suitable acid acceptors there may be mentioned pyridine or tertiary amines such as, for example, trimethylamine, tripropylamine, triethylamine and the like; triethylamine being preferred.

The conversion of the cyclic triester 4 to an inner salt 6 is typically accomplished under anhydrous conditions in the presence of an inert organic solvent at a temperature of from about 25° C. to the reflux temperature of the solvent medium, preferably from about 60° C. to about 80° C. In addition to the ethereal and halocarbon solvents mentioned supra in connection with the phosphorylation reaction, suitable solvents include polar aprotic solvents such as dimethylformamide, dimethylacetamide, hexamethylphosphoramide, acetonitrile, and the like. Acetonitrile is preferred. Selection of the tertiary amine reactant 5 is determined in part by the quaternary group desired in the resultant inner salt 6. Suitable amines 5 include both aliphatic amines such as, for example, trimethylamine, triethylamine, N,N-dimethylethylamine and the like, and heterocyclic amines such as, for example, N-methylpyrrolidine, N-ethylpyrrolidine, N-methylpiperidine, 1-methyl-4-phenylpiperazine, 1,4-dimethylpiperazine, 4-methylthiomorpholine, 4-ethylmorpholine, and the like.

Alternatively, as further illustrated by Reaction Scheme B, Formula I alkoxycarbonylalkylphospholipids wherein n is 3 or 4 and A$^2$ is —(CH$_2$)$_2$— are produced by reacting an alkanol 1a with 4-benzyloxybutyric acid or 5-benzyloxypentanoic acid 2a to form the corresponding alkyl ester 3a which is converted is converted to the 4- or 5-hydroxy derivative 4a, reacted with 2-chloro-2-oxo-1,3,2-dioxaphospholane to form a cyclic triester 5a, and then converted to the inner salt 6a by treatment with a tertiary amine 5.

The reaction of the alkanol 1a and the benzyloxybutyric or pentanoic acid 2a is generally conducted in the presence of a coupling agent and a basic acylation catalyst in an inert organic solvent at a temperature of from about −20° C. to about 50° C., preferably from about 0° C. to about 25° C. Suitable coupling agents include dicyclohexylcarbodiimide, 1-(3-dimethylaminopropyl)-3-ethylcarbodiimide hydrochloride, methiodide, and the like. Dicyclohexylcarbodiimide is preferred. Suitable acylation catalysts include 4-dimethylaminopyridine, 4-(1-pyrrolidino)pyridine and the like. 4-Dimethylaminopyridine is preferred. Suitable solvents include halogenated hydrocarbons such as, for example, chloroform, dichloromethane, 1,2-dichloroethane and the like; others solvents:ethylether, 1,2-dimethoxyethane, tetrahydrofuran. Dichloromethane is preferred. Benzyloxy-substituted alkyl esters 3a are converted to the corresponding hydroxy-substituted derivatives 4a by hydrogenation in the presence of an appropriate catalyst. The hydrogenation reaction is conducted at a temperature from about 15° C. to about 100° C. and a hydrogen gas pressure of from about 1 atmosphere to about 10 atmospheres in an appropriate solvent. Hydrogenation temperatures of from about 20° C. to about 30° C. and hydrogen gas pressures of from about 1 atmosphere to about 4 atmospheres are preferred. Among the suitable solvents for the hydrogenation reaction are alkanols, including methanol, ethanol, 2-propanol, and the like; alkanoic acids, including formic acid, acetic acid, propanonic acid and the like; and the alkyl esters of the aforementioned alkanoic acids. The preferred solvent is ethanol. Catalysts include noble metals (e.g. palladium, platinum and rhodium); with 5% palladium on carbon being preferred. Phosphorylation and subsequent quaternization of the hydroxy derivative 4a is as previously described.

Alternatively, as shown in Reaction Scheme C, Formula I compounds of this invention may be prepared by reacting a substituted alkan-1-ol 1b with an appropriate phosphorylating agent 2b followed by quaternization of the resultant phosphate diester 3b to an alkylphospholipid 5a. Included among the phosphorylating agents suitable for use herein are haloalkylphosphorodichloridates such as 2-bromoethylphosphorodichloridate, 2-chloroethylphosphorodichloridate, 2-iodoethylphosphorodichloridate, 4-bromobutylphosphorodichloridate, 6-bromohexylphosphodichloridate and the like. The phosphorylation reaction is generally conducted under anhydrous conditions in the presence of a basic organic solvent. Basic organic solvents include aliphatic and heterocyclic tertiary amines such as trimethylamine, triethylamine, pyridine, and the like. The reaction may be conducted in the presence of an appropriate co-solvent. Suitable co-solvents include etheral solvents such as diethyl ether, dioxane, tetrahydrofuran and the like; aromatic hydrocarbons such as benzene, toluene, xylene and the like; and halocarbons such as dichloroethane, chloroform, methylene chloride, and the like. Mixtures of triethylamine or pyridine and diethyl ether are preferred. The phosphorylation reaction may be conducted at a temperature of from about 0° C. to about 25° C. Preferred reaction temperatures are subject to variation depending upon the reactivity of the particular reactants employed.

Quaternization of the phosphate diester 3b to the alkylphospholipid 5b is conveniently accomplished under hydrous or anhydrous conditions utilizing the tertiary amines 4b previously described in Reaction Schemes A and B. Trimethylamine and N-methylpyrrolidine are preferred. The quaternization reaction may be conducted at a temperature of from about 20° C. to about 100° C., in the presence of an appropriate solvent. Among the suitable solvents there may be mentioned polar aprotic solvents such as dimethylacetamide, dimethylformamide, hexamethylphosphoramide, dimethyl sulfoxide, acetonitrile and the like; halocarbons such as dichloromethane, chloroform, dichloroethane and the like; etheral solvents such as diethyl ether, dioxane, tetrahydrofuran and the like, alkanols such as methanol, ethanol, 1- and 2-propanol and the like; and mixtures thereof. Acetonitrile and mixtures of acetonitrile and isopropanol are preferred. Desirably, water is present as a co-solvent. Preferably the reaction is conducted at the reflux temperature of the solvent medium and the resultant adduct is treated with silver carbonate to generate the desired product 5b.

Included among the compounds of this invention are:

1-(4-hydroxy-3,5,10-trioxa-9-oxo-4-phosphahexadec-1-yl)-1-methylpyrrolidinium, p-oxide, hydroxide, inner salt;

1-(4-hydroxy-3,5,10-trioxa-9-oxo-4-phosphatriacont-1-yl)-1-methylpyrrolidinium, p-oxide, hydroxide, inner salt;

1-(4-hydroxy-18-methyl-3,5,10-trioxa-9-oxo-4-phosphanonadecyl-1-yl)-1-methylpyrrolidinium;

1-(4-hydroxy-3,5,10-trioxa-9-oxo-4-phosphahexacos-1-yl)-N,N,N-trimethylaminium, p-oxide, hydroxide, inner salt;

1-(4-hydroxy-3,5,10-trioxa-9-oxo-4-phosphaoctadec-1-yl)-1,4-dimethylpiperidinium, p-oxide, hydroxide, inner salt;

1-(4-hydroxy-3,5,10-trioxa-9-oxo-4-phosphaheptadec-1-yl)-1-methyl-4-phenylpiperazinium, p-oxide, hydroxide, inner salt;

1-(4-hydroxy-3,5,10-trioxa-9-oxo-4-phosphaeicos-1-yl)-1-methyl-(4-morpholinium), p-oxide, hydroxide, inner salt;

1-(4-hydroxy-3,5,10-trioxa-9-oxo-4-phosphaheneicos-1-yl)-1-methyl-(4-thiomorpholinium), p-oxide, hydroxide, inner salt;

1-(9-hydroxy-7,9,14-trioxa-13-oxo-8-phosphaeicos-1-yl)-1-methylpyrrolidinium, p-oxide, hydroxide, inner salt;

1-(9-hydroxy-7,9,14-trioxa-13-oxo-8-phosphaoctacos-1-yl)-1-N,N,N-trimethylaminium, p-oxide, hydroxide, inner salt;

1-(4-hydroxy-3,5,11-trioxa-10-oxo-4-phosphaheneicos-1-yl)-1-methylpyrrolidinium, p-oxide, hydroxide, inner salt;

1-(12-aza-6-hydroxy-5,7-dioxa-11-oxo-6-phosphadocos-1-yl)-1-methylpyrrolidinium, p-oxide, hydroxide, inner salt;

1-(11-aza-4-hydroxy-3,5-dioxa-10-oxo-4-phosphaheneicos-1-yl)-1,4-dimethylpiperidinium, p-oxide, hydroxide, inner salt;

1-(12-aza-6-hydroxy-5,7-dioxa-11-oxo-6-phosphadocos-1-yl)-1-N,N,N-trimethylaminium, p-oxide, hydroxide, inner salt;

1-(14-aza-8-hydroxy-7,9-dioxa-13-oxo-8-phosphatetracos-1-yl)-1-methyl-4-phenylpiperazinium, p-oxide, hydroxide, inner salt;

1-(10-aza-4-hydroxy-3,5-dioxa-9-oxo-4-phosphaeicos-1-yl)-1-methyl-(4-thiomorpholinium), p-oxide, hydroxide, inner salt;

1-(11-aza-5-hydroxy-4,6-dioxa-10-oxo-5-phosphaheneicos-1-yl)-1-methyl-(4-morpholinium), p-oxide, hydroxide, inner salt; and 1-(10-aza-4-hydroxy-19-methyl-3,5-dioxa-9-oxo-4-phosphaeicos-1-yl)-1-methylpyrrolidinium, p-oxide, hydroxide, inner salt.

REACTION SCHEME A

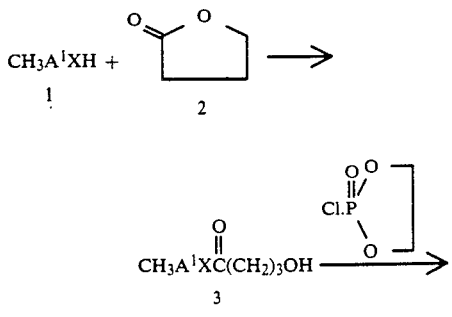

-continued
REACTION SCHEME A

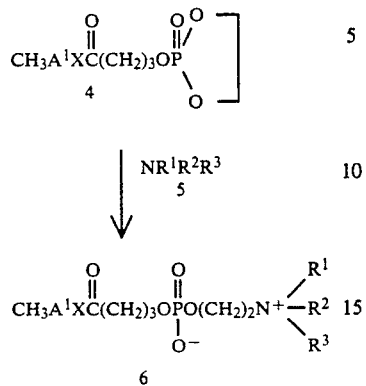

REACTION SCHEME B

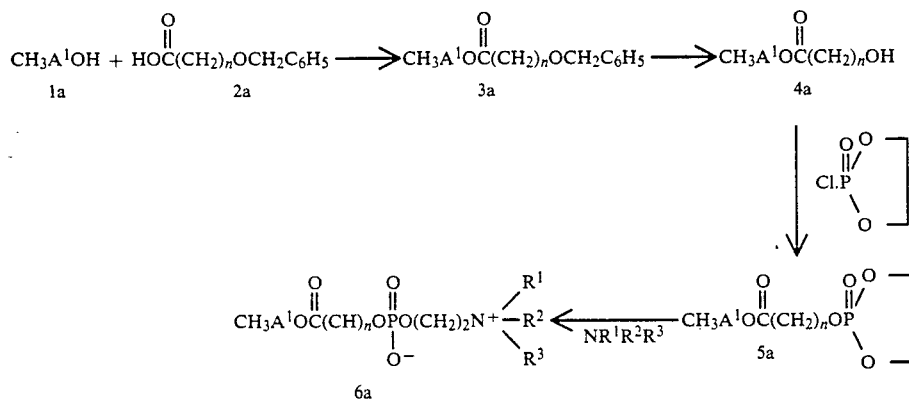

REACTION SCHEME C

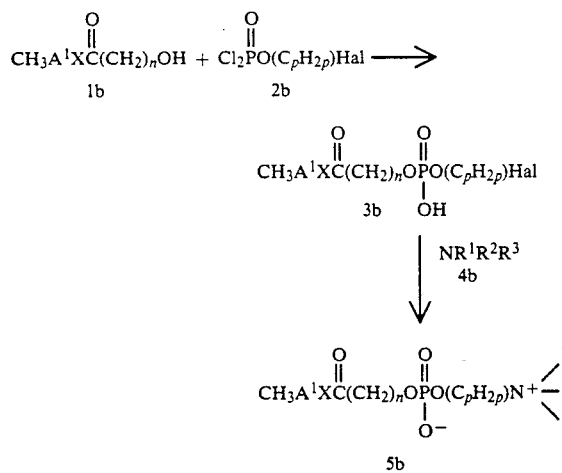

The compounds of this invention are useful as antiinflammatory agents due to their ability to suppress inflammation in mammals. The activity of the compounds is demonstrated in the carrageenan induced rat paw edema antiinflammatory assay [Proc. Soc. Exptl. Bio. Med., III, 544 (1962) and J. Pharmacol. Exp., 166, 90 (1969)].

Pursant to this procedure, inflammation is induced by a subcutaneous injection of 1% carrageenan (distilled water) into the plantar surface of the left hind paw of a group of eight rats. Test compounds are injected simultaneously with carrageenan in dimethylsulfoxide. Paw volumes (ml) are measured both before and four hours after injection by immersion of the injected paw into a mercury bath connected to a volumetric pressure transducer. Results are reported for each test group as a function of the percentage of change in paw volume from the control (carrageenan only) group.

The results of this assay for a representative compound is provided in the Table below.

TABLE

| Compound | Conc. (M) | % Change in Paw Volume from Controls |
|---|---|---|
| 1-(4-hydroxy-3,5,10-trioxa-9-oxo-4-phosphaeicos-1-yl)-1-methylpyrrolidinium, p-oxide, hydroxide, inner salt sesquihydrate | 0.1 | −60 |
| indomethacin (standard) | 0.1 | −53 |

The phospholipids of the invention are effective in the treatment of inflammation when administered orally, intraperitoneally, intraveneously or topically to a subject requiring such treatment at a dose of from about 0.1 to about 60 mg/kg of body weight per day.

It is to be understood that specific dosage regimens should be adjusted to the individual need of a particular subject and the professional judgment of the person administering or supervising the administration of the compounds of this invention. Individual requirements will depend on factors which include the particular inflammatory condition being treated and its severity; the age, weight, physical condition, and sex of the subject; as well as the particular administrative method(s) employed.

For the purpose of oral therapeutic administration, the aforesaid compounds may be incorporated with excipients, diluents and/or carriers and used in the form of tablets, troches, capsules, elixirs, suspensions, syrups, wafers, chewing gums and the like. These preparations should contain at least 0.5% of active compound, but may be varied depending upon the particular form and may conveniently be between 4% and 70% of the weight of the unit. The amount of active compound is such that a suitable dosage will be obtained. Preferred compositions and preparations according to the present invention are prepared so that an oral dosage form contains between 1.0 and 300 milligrams of the active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and nontoxic in the amounts used.

For the purposes of parenteral or topical therapeutic administration, the active compounds of the invention may be incorporated into a solution, suspension, ointment or cream. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral or topical dosage unit contains between 0.5 and 100 milligrams of active compound.

The solutions or suspensions for topical or parenteral administration may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules or disposable syringes; the topical preparation may be enclosed in multiple dose vials or dropping bottles, made of glass or plastic.

EXAMPLES

The following Examples are for illustrative purposes only and are not to be construed as limiting the invention. All temperatures are given in degrees centigrade (°C.).

Example 1

1-(4-Hydroxy-3,5,10-trioxa-9-oxo-4-phosphahexacos-1-yl)-1-methylpyrrolidinium, p-oxide, hydroxide, inner salt tetrahydrate To a stirred solution, under nitrogen, of 6.0 g of 4-hydroxybutanoic acid, n-hexadecyl ester in 150 ml of toluene and 3.0 ml of triethylamine was added, dropwise, 2.59 g of 2-chloro-2-oxo-1,3,2-dioxaphospholane. The reaction mixture was stirred overnight, filtered and concentrated. The concentrate was combined with 100 ml of anhydrous acetonitrile and 5.7 ml of N-methylpyrrolidine and heated, under nitrogen, at 60°–70° C. for 48 hours. The resulting solution was cooled to room temperature and then refrigerated. Refrigeration induced the formation of a waxy solid which was isolated by means of vacuum filtration. Preliminary purification of the solid was achieved by means of flash chromatography (silica; methanol eluent). The resulting product was taken up in dichloromethane, filtered free of silica, concentrated in vacuo, and then left open to the air overnight to equilibrate hydration states. Thus, was obtained 1.76 g (16.3%) of 1-(4-hydroxy-3,5,10-trioxa-9-oxo-4-phosphahexacos-1-yl)-1-methylpyrrolidinium, p-oxide, hydroxide, inner salt tetrahydrate as a wax.

ANALYSIS: Calculated for $C_{27}H_{54}NO_6P.4(H_2O)$: 54.80% C, 10.56% H, 2.37% N, 5.23% P. Found: 54.68% C, 10.17% H, 2.29% N, 5.65% P.

Example 2

1-(4-Hydroxy-3,5,10-trioxa-9-oxo-4-phosphaeicos-1-yl)-1-methylpyrrolidinium, p-oxide, hydroxide, inner salt sesquihydrate Step 1

To a mixture of 10 ml of gamma-butyrolactone and 40 ml of 1-decanol was added a crystal of p-toluenesulfonic acid. The reaction mixture was heated at 150° C. for 72 hours with stirring, cooled to room temperature, and then treated with 10 mg of sodium acetate. Flash chromatography (silica; 4:1 hexane:ethyl acetate eluent) afforded 5.6 g (17.7%) of 4-hydroxybutanoic acid, n-decyl ester as an oil.

ANALYSIS: Calculated for $C_{14}H_{28}O_3$: 68.81% C, 11.55% H. Found: 68.78% C, 11.56% H.

Step 2

To a stirred, chilled (0° C.) solution of 6.47 g of 4-hydroxybutanoic acid, n-decyl ester in 150 ml of sieve dried toluene and 4.45 ml of potassium hydroxide dried triethylamine was added, dropwise under nitrogen, 3.76 g of neat 2-chloro-2-oxo-1,3,2-dioxaphospholane. The reaction mixture was stirred at room temperature overnight, filtered, and concentrated at 0.1 mm Hg. The residue was combined with 150 ml of anhydrous acetonitrile and 8.27 g of N-methylpyrrolidine, and heated, under nitrogen, at 60° C. for 48 hours. The resulting solution was cooled to 0° C., and concentrated. Flash chromatography of the residue (silica; utilizing as eluents 9:1 chloroform:methanol followed by 120:30:4 chloroform:methanol:water) afforded 4.8 g (39.3%) g of 1-(4-hydroxy-3,5,10-trioxa-9-oxo-4-phosphaeicos-1-yl)-1-methylpyrrolidinium, p-oxide, hydroxide, inner salt sesquihydrate as a wax.

ANALYSIS: Calculated for $C_{21}H_{42}NO_6P.1.5H_2O$: 54.53% C, 9.81% H, 3.03% N, 6.69% P. Found: 54.58% C, 9.87% H, 3.05% N, 6.62% P.

Example 3

1-(10-Aza-4-hydroxy-3,5-dioxa-9-oxo-4-phosphaeicos-1-yl)-1-methylpyrrolidinium, p-oxide, hydroxide, inner salt monohydrate Step 1

A mixture of 15 g of decylamine, 5.48 g of gamma butyrolactone, 100 ml of toluene, and 20 mg of zinc chloride was refluxed under nitrogen for 4 days. Upon cooling the reaction mixture formed a precipitate which was recrystallized from toluene to yield 6.91 g (44.6%) of N-decyl-4-hydroxybutyramide, m.p. 74°–75° C.

ANALYSIS: Calculated for $C_{14}H_{29}NO_2$: 69.09% C, 12.01% H, 5.75% N. Found: 69.26% C, 11.87% H, 5.72% N.

Step 2

To a solution of 12 g of N-decyl-4-hydroxybutyramide and 8.18 ml of triethylamine in 245 ml of tetrahydrofuran was added, dropwise, 6.96 g of 2-chloro-2-oxo-1,3,2-dioxaphospholane. The solution was stirred at room temperature overnight, filtered and concentrated. The resulting oil was combined with 282 ml of acetonitrile and 12.5 g of N-methylpyrrolidine and refluxed for 48 hours. Filtration, concentration and azeotroping with toluene afforded a residue which was flash chromatographed (silica: 2x eluting with 9:1 chloroform:methanol followed by 120:30:4 chloroform:methanol:water; then 1x eluting with 4:1 chloroform:methanol followed by 120:30:1 and 120:30:4 chloroform:methanol:water successively) to afford 7.85 g (37%) of 1-(10-aza-4-hydroxy-3,5-dioxa-9-oxo-4-phosphaeicos-1-yl)-1-methylpyrrolidinium, p-oxide, hydroxide, inner salt, monohydrate.

ANALYSIS: Calculated for $C_{21}H_{43}N_2O_5P \cdot H_2O$: 55.73% C, 10.02% H, 6.19% N, 6.84% P. Found: 55.44% C, 9.64% H, 6.17% N, 6.26% P.

Example 4

1-(10-Aza-4-hydroxy-3,5-dioxa-9-oxo-4-phosphahexacos-1-yl-1-methylpyrrolidinium, p-oxide, hydroxide, inner salt trihydrate Step 1

A mixture of 59.45 g of hexadecylamine, 10.60 g of gamma butyrolactone, 200 ml of toluene, and 20 mg of zinc chloride was refluxed under nitrogen for three days. Upon cooling, the reaction mixture formed a precipitate which was recrystallized twice from toluene to yield 31.5 g (78.12%) of N-hexadecyl-4-hydroxybutyramide, m.p. 89.5°–90°

ANALYSIS: Calculated for $C_{20}H_{41}NO_2$: 73.34% C, 12.62% H, 4.28% N. Found: 73.54% C, 12.98% H, 4.32% N.

Step 2

To a solution of 6.31 g of N-hexadecyl-4-hydroxybutyramide and 1.95 g of triethylamine in 200 ml of toluene (sieve-dried) and 20 ml of dichloromethane, under nitrogen, was added 2.75 g of 2-chloro-2-oxo-1,3,2-dioxaphospholane. After stirring at room temperature for 24 hours, the reaction mixture was filtered and concentrated in vacuo. The concentrate was combined with 100 ml of anhydrous acetonitrile and 5.75 g of 1-methylpyrrolidine and heated, under nitrogen, at 68° C. for four days. Cooling to room temperature induced product solidification. Purification was accomplished by means of flash chromatography (silica; elution with 10:90 methanol:chloroform followed by 120:30:4 chloroform:methanol:water). The resulting product was taken up in chloroform and toluene, treated with water and concentrated in vacuo. Toluene was then added several times and the excess water was azeotroped off. Thus, there was obtained 1.09 g (9.86%) of 1-(10-aza-4-hydroxy-3,5-dioxa-9-oxo-4-phosphahexacos-1-yl)-1-methylpyrrolidium, p-oxide, hydroxide, inner salt trihydrate.

ANALYSIS: Calculated for $C_{27}H_{22}N_2O_5P \cdot 3H_2O$: 56.62% C, 10.73% H, 4.89% N, 5.40% P. Found: 56.25% C, 10.31% H, 4.73% N, 5.39% P.

Example 5

1-(10-Aza-4-hydroxy-3,5-dioxa-9-oxo-4-phosphapentadec-1-yl)-1-methylpyrrolidinium, p-oxide, hydroxide, inner salt trihydrate Step 1

A mixture of 18.71 ml of gamma-butyrolactone, 10.61 g of aminopentane, 100 ml of toluene and 20 mg of zinc chloride was refluxed for four days.

The reaction mixture was then cooled, poured into water (100 ml), and separated into organic and aqueous phases. The aqueous phase was extracted with diethyl ether (4×100 ml) and ethyl acetate (3×100 ml). The combined organic phase was dried over anhydrous magnesium sulfate, filtered and concentrated. High pressure liquid chromatography of the residue (silica gel; elution with ethyl acetate) afforded 17.25 g (81.79%) of N-pentyl-4-hydroxybutyramide, m.p. 41°–43° C.

ANALYSIS: Calculated for $C_9H_{19}NO_2$: 62.39% C, 11.05% H, 8.08% N. Found: 62.20% C, 10.90% H, 8.04% N.

Step 2

To a solution of 6.0 g of N-pentyl-4-hydroxybutyramide and 4.20 g of triethylamine in 270 ml of toluene (sieve-dried), under nitrogen, was added 4.93 g of 2-chloro-2-oxo-1,3,2-dioxaphospholane. After stirring at room temperature for 24 hours, the reaction mixture was filtered and concentrated in vacuo. The concentrate was combined with 100 ml of anhydrous acetonitrile and 10.48 g of 1-methylpyrrolindine and stirred under nitrogen for three days. The resulting mixture was then refluxed at 61° C. for two days, cooled and concentrated in vacuo. Purification of the residue was accomplished by flash chromatography (3x; silica; solvent systems as follows: (1) 90:10 chloroform:methanol followed by 120:30:4 chloroform:methanol:water (2) 120:30:4 chloroform:methanol:water and (3) 90:10 chloroform:methanol 120:30:4 chloroform:methanol:water) to afford 2.83 g (19.89%) of 1-(10-aza-4-hydroxy-3,5-dioxa-9-oxo-4-phosphapentadec-1-yl)-1-methylpyrrolinium, p-oxide, hydroxide, inner salt trihydrate.

ANALYSIS: Calculated for $C_{16}H_{53}N_2O_5P \cdot 3H_2O$: 45.92% C, 9.39% H, 6.69% H, 7.40% P. Found: 46.28% C, 8.99% H, 6.68% H, 7.23% P.

Example 6

1-(4-Hydroxy-3,5,10-trioxa-9-oxo-4-phosphaeicos-1-yl)-1-trimethylaminum, p-oxide, hydroxide, inner salt 2.5 hydrate A solution of 6 g of 4-hydroxybutanoic acid, n-decyl ester, 4.5 ml of of triethyl amine, 3.8 g of 2-chloro-2-oxo-1,3,2-dioxaphospholane and 150 ml toluene was stirred at room temperature overnight. Concentration afforded a gum which was dissolved in 120 ml of acetonitrile and placed in a pressure reactor. The reactor was cooled in a dry ice/methanol bath and approximately 15 g of trimethylamine was condensed into it. The reactor was sealed and warmed to 60° and stirred for 2 days. Concentration gave a gum which was flash chromatographed using 9:1 chloroform:methanol followed by 120:30:4 chloroform:methanol:water as eluents to yield 6.3 g (57%) of 1-(4-hydroxy-3,5,10-trioxa-9-oxo-4-phosphaeicos-1-yl)-1-trimethylaminum, p-oxide, hydroxide, inner salt 2.5 hydrate, as a gum.

ANALYSIS: Calculated for $C_{19}H_{40}NO_6P \cdot 2.5H_2O$: 50.20% C, 9.98% H, 3.08% N, 6.81% P. Found: 50.33% C, 9.76% H, 3.15% N, 7.27% P.

What is claimed is:

1. A compound of the formula

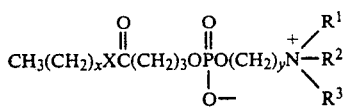

wherein X is a bivalent radical of the formula —O— or —N(H)—; $R^1$ is an alkyl radical having up to 6 carbon atoms, inclusive; $R^2$ and $R^3$ taken together with $R^1$ and the nitrogen atom to which they are attached form a group of the formula

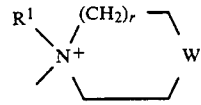

wherein r is 0 or 1, W is oxygen, $CH_2$, sulfur or $N(R^4)$ wherein $R^4$ is an alkyl radical having up to 6 carbon atoms, inclusive, or aryl; the term "aryl" in each occurrence signifying a phenyl radical optionally substituted by one or more substituents selected from the group consisting of alkyl, alkoxy, halogen, hydroxy or trifluoromethyl; x is an integer having a value from 0 to 20, inclusive; and y is an integer having a value from 0 to 6, inclusive, and optical antipodes thereof.

2. A pharmaceutical composition comprising an effective inflammation alleviating amount of a compound as defined in claim 1 and a suitable carrier therefor.

3. A method of treating inflammation comprising administering to a patent in need of inflammation alleviation, an inflammation alleviating effective amount of a compound as defined in claim 1.

* * * * *